US009446076B2

(12) United States Patent
Gaussin et al.

(10) Patent No.: US 9,446,076 B2
(45) Date of Patent: Sep. 20, 2016

(54) PHARMACEUTICAL COMPOSITION FOR THE TREATMENT OF HEART DISEASES

(75) Inventors: Vinciane Gaussin, Thousand Oaks, CA (US); Roland Gordon-Beresford, La Hulpe (BE); Christian Homsy, Lasne (BE)

(73) Assignee: CARDIO3 BIOSCIENCES S.A., Mont-Saint-Guibert (BE)

( * ) Notice: Subject to any disclaimer, the term of this patent is extended or adjusted under 35 U.S.C. 154(b) by 0 days.

(21) Appl. No.: 13/321,224

(22) PCT Filed: May 20, 2010

(86) PCT No.: PCT/EP2010/057004
§ 371 (c)(1),
(2), (4) Date: Feb. 3, 2012

(87) PCT Pub. No.: WO2010/133686
PCT Pub. Date: Nov. 25, 2010

(65) Prior Publication Data
US 2012/0128638 A1 May 24, 2012

(30) Foreign Application Priority Data
May 20, 2009 (WO) ............... PCT/EP2009/056197

(51) Int. Cl.
*A61K 35/34* (2015.01)
(52) U.S. Cl.
CPC ................................. *A61K 35/34* (2013.01)
(58) Field of Classification Search
CPC ...................................................... A61K 35/34
USPC ............................. 424/93.7, 93.1; 435/374
See application file for complete search history.

(56) References Cited

U.S. PATENT DOCUMENTS

| | | | | |
|---|---|---|---|---|
| 6,045,990 | A * | 4/2000 | Baust et al. | 435/1.1 |
| 6,632,666 | B2 * | 10/2003 | Baust et al. | 435/374 |
| 6,921,633 | B2 * | 7/2005 | Baust et al. | 435/1.3 |
| 8,642,255 | B2 * | 2/2014 | Nicoud et al. | 435/2 |
| 2004/0071665 | A1 | 4/2004 | Xiao et al. | |
| 2008/0019944 | A1* | 1/2008 | Terzic et al. | 424/93.1 |
| 2008/0276643 | A1 | 11/2008 | Heroux et al. | |
| 2011/0014701 | A1* | 1/2011 | Ghosh | 435/374 |

FOREIGN PATENT DOCUMENTS

| | | | |
|---|---|---|---|
| EP | 2100954 A1 * | 9/2009 | |
| RU | 2458797 C2 | 6/2008 | |
| WO | 2006/015127 A2 | 2/2006 | |
| WO | 2006/080434 A1 | 8/2006 | |
| WO | 2008/0147057 A1 | 4/2008 | |
| WO | 2008083962 A1 | 7/2008 | |
| WO | 2008/109839 A1 | 9/2008 | |
| WO | 2009/151907 A2 | 12/2009 | |
| WO | 2010/125159 A1 | 11/2010 | |

OTHER PUBLICATIONS

Baust et al., Modulation of the cryopreservation cap: Elevated survival with reduced dimethyl sulfoxide concentration. Cryobiology, vol. 45 (2002) pp. 97-108.*
Mathew, A., Similarities and differences between CryoStor® and HypoThermosol®. BioLife Solutions, personal communication, May 1, 2014.*
Zwi et al., Cardiomyocyte differentiation of human induced pluripotent stem cells. Molecular Cardiology, vol. 120 (online Sep. 28, 2009) pp. 1513-1523.*
Abdel-Latif et al., Arch Intern Med, 167:989-997 (2007). "Adult Bone Marrow-Derived Cells for Cardiac Repair."
Behfar et al. Nature Clinical Practice, 3(Suppl. 1):S78- S82 (2006). "Derivation of a cardiopoietic population from human mesenchymal stem cells yields cardiac progeny."
Behfar et al., JEM, 204(2):405-420 (2007). "Cardiopoietic programming of embryo stem cells for tumor-free heart repair."
Behfar et al., J Mol Cell Cardiol, 45(4):523-529 Author Manuscript (2008). "Guided Stem Cell Cardiopoiesis: Discovery and Translation."
Matsumura et al., Cell Transplantation, 19:691-699 (2010). "Polyampholytes as Cyroprotective Agents for Mammalian Cell Cryopreservation."
Morley et al., Journal of Cellular Physiology, 156:219-225 (1993). "The Differentiation Inducer, Dimethyl Sulfoxide, Transiently Increases the Intracellular Calcium Ion Concentration in Various Cell Types."
Pal et al., Arch Toxicol, 86:651-661 (2012). "Diverse effects of dimethyl sulfoxide (DMSO) on the differentiation potential of human embryonic stem cells."
Peng et al., Physiol Genomics, 9:145-155 (2002). "Microarray analysis of global changes in gene expression during cardiac myocyte differentiation."
Sigma-Aldrich, Biofiles, 5(4):1-24 (2010). "Cyropreservation."
Baust, "Advances in Media for Cryopreservation and Hypothermic Storage" BioProcess International 46-56 (Jun. 2005).
Mather (Ed.), "Methods in Cell Biology, Stem Cell Culture" vol. 86(Chap. 10):241-267 (2008).
Oh et al., "Cardiac Progenitor Cells from Adult Myocardium: Homing, Differentiation, and Fusion After Infarction" PNAS 100(21):12313-12318 (2003).
Van Buskirk et al., "Hypothermic Storage and Cryopreservation" BioProcess International 42-49 (Nov. 2004).

* cited by examiner

*Primary Examiner* — Laura Schuberg
*Assistant Examiner* — Kara Johnson
(74) *Attorney, Agent, or Firm* — Nixon Peabody LLP

(57) ABSTRACT

The present invention is related to a pharmaceutical composition comprising cells committed to the generation of heart tissue and at least one pharmaceutically acceptable excipient produced according to internationally recognized standards for pharmaceutical product manufacture, a process for the manufacture of such a pharmaceutical composition and a kit for the administration of said pharmaceutical composition which comprises a container containing said pharmaceutical composition.

42 Claims, 1 Drawing Sheet

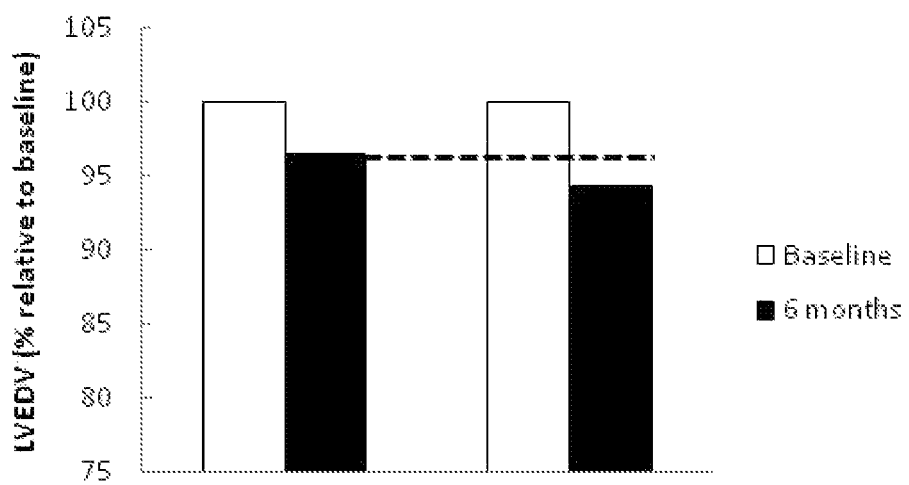
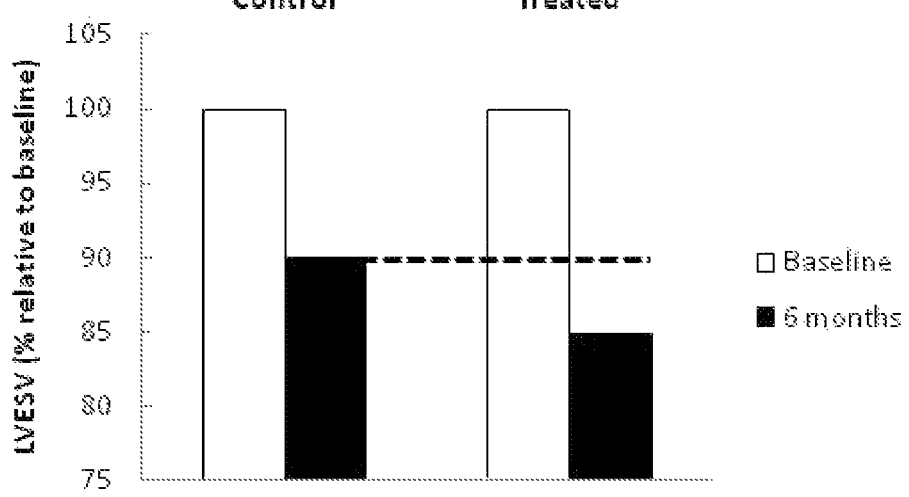
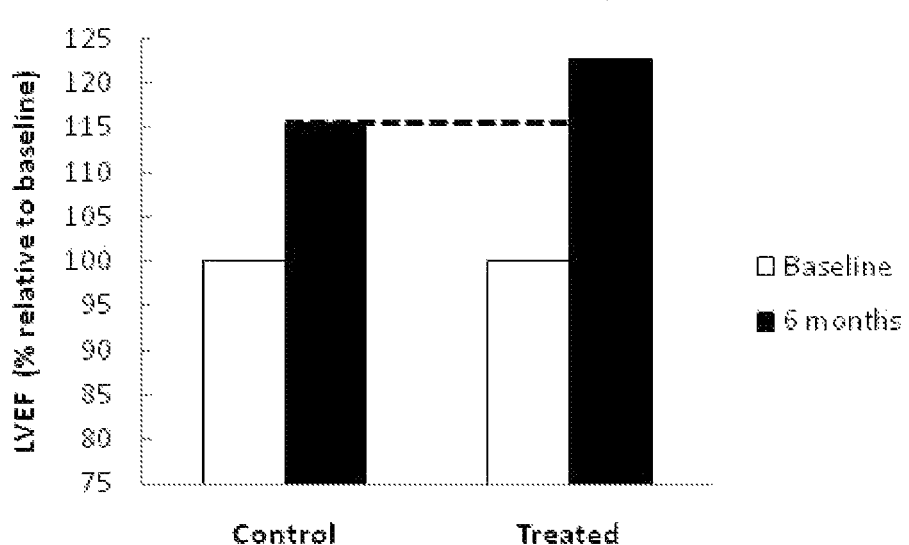

PHARMACEUTICAL COMPOSITION FOR THE TREATMENT OF HEART DISEASES

CROSS REFERENCE TO RELATED APPLICATIONS

This application is a 35 U.S.C. §371 National Phase Entry Application of International Application No. PCT/EP2010/057004 filed May 20, 2010, which designates the U.S., and which claims benefit of International Application No. PCT/EP2009/056197 filed May 20, 2009, the contents of which are incorporated herein by reference in their entireties.

FIELD OF THE INVENTION

The present invention relates to the treatment of heart disease disorders or predispositions of a disorder through delivery of a pharmaceutical composition to an individual in need. In particular, it discloses a pharmaceutical composition comprising cells committed to the generation of heart tissue and at least one pharmaceutically acceptable excipient, contained in a container in a way to allow cell survival and transportation to locations worldwide, convenient handling by staff for delivery to the recipient, wherein said cells are produced according to internationally recognized standards for pharmaceutical product manufacture.

STATE OF THE ART

Regenerative cell therapies are particularly relevant for diseases in which organs are compromised in such a way that tissue reconstruction is required, e.g. to restore the morphology as well as the function of a diseased organ, or when physiological repair mechanisms are impaired. The heart is a terminally differentiated organ and massive loss of cardiomyocytes such as in heart attack causes irreversible damages, hence the need for repair. In addition heart disease is a leading cause of mortality worldwide. Cell therapy for heart repair is a challenge of utmost importance.

Clinical experience with cell therapy has been based on adult stem cells delivered in an unaltered state. First generation biologics are naive human stem cells, identified as readily accessible cytotypes. It has been shown that a few individuals improve on delivery of naive human stem cells. The state of the art in the field of naive cell transplantation in the heart of humans was described inter alia in the review carried by Abdel-Latif A. et al. 'Adult bone marrow-derived cells for cardiac repair: a systematic review and meta-analysis.' Arch Intern Med. (2007) 167:989-997, and citations therein. In the hope of improving clinical outcome, the concept of second-generation stem cell therapies was developed and consists in improving the cardio-generative potential of naive stem cells prior to delivery to the patient.

In order to explore ways of improving cardio-generative potential of a cell, fundamental research first used mouse embryonic stem cells (hereinafter mESCs) to decipher complex signaling pathways involved during cardiac differentiation. This research led to the identification of cardiogenic substances which, in contact with a cell, improves the ability of said cell to differentiate into a cardiopoietic cell. The cardiopoietic cell is an intermediate cell phenotype where the cell is committed to the generation of heart tissue but not yet fully differentiated. Key milestones in basic research in the field of cardiac regeneration are disclosed in:

Behfar et al. 'Derivation of a cardiopoietic population from human mesenchymal stem yields progeny', Nature Clin. Pract., Cardiovasc. Med. (2006) 3: S78-S82, Behfar et al., 'Cardiopoietic programming of embryonic cells for tumor-free repairs', J. Exp. Med. (2007) 204: 405-420, and WO 2006/015127, US 2008/0019944 and WO 2009/151907, all to Mayo Foundation for Medical Education and Research, Terzic A. and Behfar A.

The above authors, applicant and inventors showed that the differentiation of mESCs into cells committed to the generation of heart tissue can be initiated when mESCs are cultured in contact with so-called 'cocktails' of cardiogenic substances, i.e. compositions containing cardiogenic factors in solution. As disclosed in WO2006/015127, when mESCs-derived cardiopoietic cells are delivered into chronically infarcted murine hearts, heart repair can be achieved. Thus, it has been made known that mESCs-derived cardiopoietic cells could show beneficial in regenerating heart tissue. However, the tumourigenic risk associated with ESCs raises safety issues to translate these basic findings for therapeutic use. Furthermore, the experiments were carried out in mice in the laboratory setting with mESC-derived cardiopoietic cells harvested from culture, suspended in culture medium in a laboratory tube, and promptly used thereafter within the same facility.

Adult stem cell therapy is considered to be devoid of tumourigenic risk. Identification of a source of stem cells with no documented tumourigenic risk and suitable for derivation into cardiopoietic cells was described in Behfar et al. 'Derivation of a cardiopoietic population from human mesenchymal stem yields progeny', Nature Clinical Practice, Cardiovascular Medicine (2006) 3:S78-S82. In US 2008/0019944 cardiopoietic cells obtained from mesenchymal stem cells are described.

The authors, applicant and inventors also disclosed that differentiation of human adult mesenchymal stem cells into cardiopoietic cells can be achieved using a cocktail of cardiogenic factors (WO 2009/151907).

The state of the art in the field of cell transplantation in the heart of humans was described inter alia in the review carried by Abdel-Latif A. et al. 'Adult bone marrow-derived cells for cardiac repair: a systematic review and meta-analysis.' Arch Intern Med. (2007) 167:989-997, and citations therein. In another review by Behfar et al. 'Guided stem cell cardiopoietic: Discovery and translation' J. Mol. and Cell. Cardiology (2008) 45: 523-529, the concept of using cardiopoietic cells for heart regeneration was also discussed.

Moving from bench to bedside is usually a challenge for the pharmaceutical industry. In this case, this challenge has been particularly difficult to overcome because of the biological features of the cells committed to the generation of heart tissue and the absolute need to maintain these features till delivery to an individual when the individual is not present near the premises of the manufacturing premises.

The present invention solves this problem by disclosing a method for industrially producing a pharmaceutical composition containing cells committed to the generation of heart tissue and at least one pharmaceutically acceptable excipient according to internationally recognized standards for pharmaceutical product manufacture, a method for cell preservation and packaging that allows differed use whilst maintaining the features of cells committed to the generation of heart tissue, their survival, transportation to locations worldwide, convenient handling by staff for delivery to the recipient.

DEFINITIONS

Within the frame of the present document, and unless indication of the contrary, the terms designated below between quotes have the following definitions.

'BMMSC' designates bone marrow mesenchymal stem cells. 'hBMMSC' designates such BMMSCs of human origin.

'Cardiopoietic cells' are an intermediate cell phenotype, i.e. committed to the generation of heart tissue but not yet fully differentiated. Cardiopoietic cells are characterized by nuclear translocation of NRx2.5 and MEF2C, combined to the absence of sarcomeric proteins (Behfar et al. *'Derivation of a cardiopoietic population from human mesenchymal stem yields progeny'*, Nature Clin. Pract., Cardiovasc. Med. (2006) 3: S78-S82). Cardiopoietic cells retain a proliferative capacity. Cardiopoietic cells can be derived from stems cells including for example, human adult mesenchymal stem cells, human embryonic stem cells (provided their production implies no human embryo destruction), embryonic-like stem cells, inducible pluripotent stem cells, or any other adapted source.

A 'cardiogenic cocktail' or 'cocktail' designates a composition containing at least two cardiogenic substances.

A 'cardiogenic substance' is a substance which, in contact with a cell, improves the ability of said cell to differentiate into a cardiopoietic cell.

'Confluence' designates the state in which cells have grown to maximum capacity within a certain amount of space. At this point contact with other cells causes them to inhibit growth.

The 'effective amount' means a sufficient amount of the pharmaceutical composition to provide the desired therapeutic or physiological effect or outcome. Such an effect or outcome includes the repair, maintenance, regeneration, augmentation of heart tissue or improvement of heart function. Undesirable effects are sometimes manifested along with the desired therapeutic effect; hence, a practitioner balances the potential benefits against the potential risks in determining what an appropriate 'effective amount' is. This amount may vary from subject to subject, depending for example on the subject age, general condition, genetic and epigenetic variability and the like, and the mode of administration. Thus, it may not be possible to specify an exact 'effective amount'. However, an appropriate 'effective amount' in any individual case may be determined by one of ordinary skill in the art before or during the administration procedure of the pharmaceutical composition, for example by delivering the highest amount possible without undesirable effect during delivery of the pharmaceutical composition.

'Excipient' is an inactive substance used as a carrier for the active ingredients of a medication. In many cases, an "active" substance may not be easily administered and absorbed by the human body; in such cases the substance in question may be dissolved into or mixed with an excipient. In addition to their use in the single-dosage quantity, excipients can be used in the manufacturing process to aid in the handling of the active substance concerned. Depending on the route of administration, and form of medication, different excipients may be used. To stabilize the active ingredient, excipients are added, ensuring that the active ingredient stays "active", and, just as importantly, stable for a sufficiently long period of time that the shelf-life of the product makes it competitive with other products.

'Proliferative capacity' designates within the frame of this document, an increase of cell number.

'Viability' means within the frame of this document the feature for cells of not taking up the trypan blue dye, thereby demonstrating cell membrane integrity.

The terms 'subject', 'recipient' and 'patient' are used interchangeably herein and refer unless explicitly stated to any human or mammal in need of treatment for a cardiac disease or disorder with the hereby disclosed pharmaceutical composition. Subjects also include those at risk of having such a cardiac disease or disorder.

As used in the subject specification, the singular forms 'a', 'an' and 'the' include plural aspects unless the context clearly dictates otherwise. Thus, for example, reference to 'a stem cell' includes a single cell, as well as two or more cells; reference to 'an agent' or 'a reagent' includes a single agent or reagent, as well as two or more agents or reagents; reference to 'the invention' or 'an invention' includes single or multiple aspects of an invention; and so forth.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below.

SUMMARY OF THE INVENTION

In the following detailed description, numerous details are set forth in order to provide a thorough understanding of the present claimed subject matter. However, it will be understood by those skilled in the art that the claimed subject matter may be practiced without these specific details. In other instances, well-known methods, procedures, components, and alike have not been described in detail so as to not obscure the claimed subject matter.

The present invention relates to a pharmaceutical composition comprising cells committed to the generation of heart tissue and at least one pharmaceutically acceptable excipient. Cells committed to the generation of heart tissue are preferably produced according to internationally recognized standards for pharmaceutical product manufacture. Most preferably, said pharmaceutically acceptable excipient is a preservation solution. Preferably, the preservation solution is chosen in the group comprising preservation solutions which allow cryopreservation at temperatures between −196° C. and 0° C. and preservation solutions which allow preservation at temperatures between 0° C. and +40° C. Preferably, the preservation solution is a preservation solution which may contain ions, pH buffers, impermeants, colloids and metabolites, dimethylsulfoxide (DMSO), glycerol, sucrose, serum albumin, trehalose, or any combination thereof. Preferably, ions are selected from the group consisting of $Na^+$, $K^+$, $Ca^{2+}$, $Mg^{2+}$, $Cl^-$ and combinations of said ions. Preferably, pH buffers are selected from the group consisting in $H_2PO_4^-$, $HCO_3^-$, (4-(2-hydroxyethyl)-1-piperazineethanesulfonic acid) (HEPES) and mixtures thereof. Preferably, impermeants are selected from the group consisting of lactobionate, sucrose, mannitol, glucose and combinations thereof. Preferably, the colloid is Dextran-40. Preferably, the metabolites are selected from the group consisting of adenosine, glutathione, and combinations thereof. Preferably, said at least one pharmaceutically acceptable excipient further comprises at least one component selected from the group consisting of growth factors, cytokines, proteins involved in organogenesis signalling, pharmaceuticals, platelet lysate, serum, isotopes, means for tracing cells in vivo, diluents, lubricants, matrix or scaffold materials, and combinations thereof.

Preferably, cells committed to the generation of heart tissue may be stem cells or cells committed to the generation of heart tissue derived from stem cells. Preferably, stem cells are selected in the group consisting of adult stem cells, embryonic stem cells, induced pluripotent stem cells (IPS), marrow-isolated adult multilineage inducible cells (MI-AMI), resident cardiac stem cells, vegetal stem cells, or any combination thereof. Preferably, stem cells are mesenchymal stem cells harvested from a suitable tissue source selected in the group consisting of bone marrow, adipose tissue, umbilical cord blood, amniotic fluid, menstrual fluid, blood. Preferably, cells committed to the generation of heart tissue are mammalian cells. Preferably, mammalian cells are selected in the group consisting of humans, cats, dogs, pigs, horses, mice, rats, hamsters and other mammals. Preferably, said cells are autologous cells, allogeneic cells, xenogenic cells, or any combination thereof.

Preferably, cells committed to the generation of heart tissue are cardiopoietic cells. Preferably, cardiopoietic cells can be derived from stems cells including for example, from human adult mesenchymal stem cells, human embryonic stem cells (provided their production implies no human embryo destruction), embryonic-like stem cells, inducible pluripotent stem cells, cardiac resident stem cells or any other adapted source or combination thereof.

Preferably, said composition contains no detectable non-cardiopoietic cells, including but not limited to cardiomyocytes, hematopoietic cells, endothelial progenitor cells, adipoblasts, adipocytes, chondroblasts, chondrocytes, osteoblasts osteocytes, neuroblasts and neurocytes. Preferably, the contents of total non-cardiopoietic cells is between 0% and 50% of the total number of cells, preferably between 0% and 15% of the total number of cells. Preferably, the contents of each category of non-cardiopoietic cells is between 0% and 50% of the total number of cells, preferably between 0% and 15% of the total number of cells.

The invention also relates to a pharmaceutical composition for use for the treatment of ischemic cardiomyopathy, acute myocardial infarction, chronic myocardial infarction, heart failure of non-ischemic origin, heart failure of ischemic origin, congenital cardiomyopathy, or combination thereof.

The invention also relates to a process for the manufacture of a pharmaceutical composition which comprises the following steps:
   obtaining cells from which cells committed to the generation of heart tissue can derive;
   culturing said cells in conditions which allow to obtain cells committed to the generation of heart tissue;
   harvesting said committed cells;
   adding to said committed cells at least one pharmaceutically acceptable excipient.

Preferably, the process of the invention is conducted according to internationally recognized standards for pharmaceutical product manufacture, which comprises taking samples at any step of the process for the purpose of performing quality control operations. Most preferably, the process of the invention is conducted according to internationally recognized standards for pharmaceutical product manufacture, which comprises taking samples at the last step of cell culture for the purpose of performing quality control of the active substance.

Preferably, quality control criteria of the active substance comprise at least one test selected from the group consisting of identity test, homogeneity test, purity test and combinations thereof. Preferably, when cells committed to the generation of heart tissue are cardiopoietic cells, identity of said cardiopoietic cells corresponds to an observed increase in expression level of at least one gene in the group consisting of NRx2.5, Tbx5, MEF2C, GATA4, GATA6, Mesp1, FOG1, FOG2, Flk1 and homologues thereof. Preferably, the increase of gene expression is a minimum 2-fold as determined by qPCR method, as compared to a reference. Preferably, when cells committed to the generation of heart tissue are cardiopoietic cells, identity of said cardiopoietic cells is considered fulfilled by the observed presence of at least one polypeptide species chosen from the group consisting of NRx2.5, Tbx5, MEF2C, GATA4, GATA6, Mesp1, FOG1, FOG2, Flk1 and homologues thereof, as compared to a reference, and either NRx2.5 or MEF2C or both being further translocated to the nuclei of the cardiopoietic cells. Preferably, the observed presence is shown by immuno-labelling with at least one antibody in the group consisting of anti-NRx2.5, anti-Tbx5, anti-MEF2C, anti-GATA4, anti-GATA6, anti-Mesp1, anti-FOG1, anti-FOG2, anti-Flk1, and homologues thereof. Preferably, homogeneity is fulfilled when at least 50% in a given sample are cardiopoietic cells. Preferably, homogeneity is fulfilled when at least 50%, most preferably at least 85%, in a given sample are cardiopoietic cells. Preferably, presence of mesenchymal stem cells amongst harvested cells is shown by positive immuno-labelling with an antibody against a surface marker selected in the group consisting of CD105, CD90, CD133, CD105, CD166, CD29, and CD44, and lack of detectable immune-labelling with an antibody against a surface marker selected in the group consisting of CD14, CD34, and CD45. Preferably, purity is not fulfilled with increased in expression level of the CD34, FABP4, osteocalcin, nestin, Sox9, and MYH7 genes and homologues thereof two-fold or greater when compared to a reference. Preferably, the increase of gene expression is determined by qPCR method, as compared to a reference. Preferably, purity is not fulfilled with increased number of non-cardiopoietic cells, including but not limited to cardiomyocytes, hematopoietic cells, endothelial progenitor cells, adipoblasts, adipocytes, chondroblasts, chondrocytes, osteoblasts osteocytes, neuroblasts and neurocytes, as shown by immuno-labelling. Preferably, said reference consists of non-cardiopoietic cells. Preferably, said reference consists of cells cultured in the absence of any cardiogenic substance. Preferably, culturing conditions include using a bioreactor which comprises immobilising or encapsulating said cells on particles or on a matrix and passing cell culture media through the bed of particles or matrix.

The invention also relates to a method for the treatment of heart disease disorders or predisposition of a disorder wherein the pharmaceutical is delivered into an individual in an effective amount. Preferably, the individual shows an insufficiency of the cardiovascular system. Preferably, the individual suffers from ischemic cardiomyopathy, myocardial infarction, heart failure of ischemic origin, or heart failure of non-ischemic origin, congenital cardiomyopathy, or combination thereof.

Preferably, the pharmaceutical composition is delivered using a route of administration selected in the group consisting of intra-myocardial, intra-cardiac, intra-coronary, intra-muscular, sub-cutaneous, intra-peritoneal, in utero, parenteral, or systemic. Preferably, the pharmaceutical composition is injected intramyocardially using a catheter, a syringe, or combination thereof.

Cells from which cells committed to the generation of heart tissue can derive may be put into contact with at least one cardiogenic substance, which may be selected from the group consisting of TGF-β1, TGF-β2, TNF-α, BMP-1, BMP-2, BMP-4, BMP-6, FGF-2, FGF-4, FGF-5, FGF-12, FGF-13, FGF-15, FGF-20, leukaemia inhibitory factor (LIF), VEGF-A, VEGF-C, insulin-like growth factor 1

(IGF-1), interleukin 6 (IL-6), Activin A, α thrombin, retinoic acid, cardiotrophin 1, cardiogenol C, and combinations thereof.

A great number of cardiogenic cocktails may be used. The list given below is not limitative. One may use for instance a cocktail of cardiogenic substances that comprises TGFβ-1, BMP4, α-thrombin, a compound selected from the group consisting of Cardiotrophin and IL-6, and a compound selected from the group consisting of Cardiogenol C and retinoic acid. Another cocktail may comprise TGFβ-1, BMP4, α-thrombin, Cardiotrophin and Cardiogenol C. Still another cocktail may comprise at least one compound selected from the group consisting of FGF-2, IGF-1, Activin-A, TNF-α, FGF-4, LIF, VEGF-A and combinations thereof. They may also comprise FGF-2, IGF-1 and Activin-A. Other preferred cocktails comprise Activin-A, FGF-2, IL-6, IGF-1 and retinoic acid. Other cocktails can lack at least one compound chosen in the group consisting of TNF-α, FGF-4, LIF, and VEGF-A.

When one of the following compounds is present in a cocktail, it may be present in an amount of between 1 and 5 ng of said TGFβ-1 per ml, between 1 and 10 ng of said BMP4 per ml, between 0.5 and 5 ng of said Cardiotrophin per ml, between 0.5 and 5 units of said α-thrombin per ml, and between 50 and 500 nM of said Cardiogenol C, between 1 and 10 ng of said FGF-2 per ml, between 10 and 100 ng of said IGF-1 per ml, between 1 and 50 ng of said Activin-A per ml, between 1 and 50 ng of said TNF-α per ml, between 1 and 20 ng of said FGF-4 per ml, between 10 and 100 ng of said IL-6 per ml, between 1 and 10 units of said LIF per ml, between 1 and 50 ng of said VEGF-A per ml, between 0.1 and 1.0 µM of said retinoic acid per ml.

A particular cocktail type comprises recombinant TGFβ-1 (2.5 ng/ml), BMP4 (5 ng/ml), Cardiotrophin (1 ng/ml), Cardiogenol C (100 nM), used in a combinatorial fashion. Particularly preferred cocktails comprises such compounds and further comprise α-thrombin, (1 U/ml), FGF-2 (10 ng/ml), IGF-1 (50 ng/ml) and Activin-A (5 ng/ml).

Other preferred cocktails comprise recombinant TGFβ-1 (2.5 ng/ml), BMP4 (5 ng/ml), Activin-A (5 ng/ml), FGF-2 (10 ng/ml), IL-6 (100 ng/ml), Factor-IIa (hα-thrombin, 1 U/ml), IGF-1 (50 ng/ml), and retinoic acid (1 µM) used in a combinatorial fashion.

The cocktail may be diluted in a medium containing compounds selected from the group consisting of foetal calf serum, human serum, platelet lysate, platelet-derived growth factor, and mixtures thereof and compounds selected. [0001] The present invention also relates to a kit for the administration of a pharmaceutical composition which comprises a container containing said pharmaceutical composition. Preferably said container is a biocompatible container that allows cell survival and transportation worldwide, convenient handling by staff for delivery to the recipient. Preferably said container is hermetically closed. Preferably said container is compatible with the excipient and conditions of preservation. Preferably said container is a closed glass container. Preferably said container has a piercable septum cap. Preferably said piercable septum cap allows a vial adapter that includes a luer activated valve to draw fluid from the container. Preferably said piercable septum cap can be accessed with a needle. Preferably said pharmaceutical composition is stored in a hermetically closed container suitable for cryopreservation. Preferably, shelf-life of pharmaceutical composition in said container is at least 48 hours, preferably 72 hours. Preferably, said kit further comprises at least one catheter. Preferably, said kit further comprises at least one syringe.

BRIEF DESCRIPTION OF THE DRAWING

FIGS. 1A-1C depict Left Ventricular (LV) End Diastolic Volume (LVEDV, FIG. 1A), LV End Systolic Volume (LVESV, FIG. 1B), and LV Ejection Fraction (LVEF, FIG. 1C), that were measured at baseline and 6 months thereafter in subjects randomly assigned to control (n:8) and treated (n:9) groups, Results were normalized to baseline.

DETAILED DESCRIPTION OF THE INVENTION

Example

Start of manufacture: Human bone marrow sample having been harvested from the iliac crest of a patient and meeting minimum quality criteria are cultured at 37° C./5% $CO_2$ incubators in 175-$cm^2$ flasks to purify BMMSCs. Minimum quality criteria include negative serology test of the donor (at least HIV ½, syphilis, HBV, HCV), bone marrow transportation temperature control between collection site and manufacturing site, total volume, recording the presence and volume of blood clots, and the absence of bacterial contamination. After 24 hours, bone marrow and cellular debris are carefully discarded from the flasks. Adherent BMMSCs are washed with phosphate buffer saline (PBS), culture medium is added, and culture is resumed until initial passage P0 with change of medium every four to six days.

P0—Initial expansion from colonies to cell layer: An initial passage (P0) is performed to dissociate colonies and to allow them to expand and form a monolayer. Cells are seeded at a one-to-one ratio in 175-$cm^2$ flasks and allowed to expand and form a monolayer for up to 6 days. Confluence determines timing for the next passage. This step may be skipped if BMMSCs spontaneously form a monolayer with no detectable colonies. The process continues with similar passages numbered 'P0' followed by a sequential letter until a minimum of $50 \times 10^6$ cells is obtained. Parameters such as cell density at seeding and confluence-triggered passages are defined. It is the number of cells obtained at a passage that determines the container size that should be used for seeding in order to optimize yield and to avoid contact inhibition. In-process control testing in the P0 phase includes cell number and percent viability.

P1—Start of cardiogenic cocktail treatment: Cells are cultured for 5 days in culture medium and a cardiogenic cocktail. For instance, cardiogenic cocktails such as described in WO2006/015127, WO2009/151907 and Behfar et al. 'Derivation of a cardiopoietic population from human mesenchymal stem yields progeny', Nature Clinical Practice, Cardiovascular Medicine, March 2006 vol. 3 supplement 1, pages S78-S82) may be used.

P2—End of cardiogenic cocktail treatment: The medium containing the cardiogenic cocktail is discarded. The culture now contains cardiopoietic cells. The culture is passaged and seeded in new containers with culture medium to allow for additional expansion phases as needed.

P3—Expansion and harvest: The following passages are numbered 'P3' followed by a sequential letter. Cells are passaged when optimal confluence is reached, and repeated until the number of cells obtained is between $600 \times 10^6$ and $1200 \times 10^6$ cells. When this criterion is met, the cells are harvested. This step involves a final trypsinization followed by washing and concentration steps by centrifugation. The final wash is performed in a cell preservation solution. Suitably, the preservation solution employed may be similar to standard organ and biological tissue preservation aqueous cold storage solutions such as HypoThermosol-FRS® from BioLifeSolutions (Bothell, Wash.).

The cell concentrate is then transferred into a biocompatible container (in this example glass bottle of Type I, Ph. Eur.) and preservation solution added to reach a total volume of 10 ml and a cellular concentration in the range of $60 \times 10^6$ to $120 \times 10^6$ cells/ml. This finalizes the manufacture of the pharmaceutical composition.

The pharmaceutical composition release criteria typically include cellular identity, homogeneity and purity that are combined with manufacture parameters that confirm the absence of adventitious contamination (asepsis, low level of endotoxin, and mycoplasma not added by the process).

It is worth noting that without any prejudice to present invention, other methods of production of cardiopoietic cells could be envisaged instead of the use of cardiogenic substances.

In this example, the preservation medium is HypoThermosol-FRS® from BioLifeSolutions (Bothell, Wash.). HypoThermosol-FRS contains ions (100 mM Na+, 42.5 mM K+, 0.05 mM Ca2+, 5 mM Mg2+, 17.1 mM Cl−); pH buffers (10 mM H2PO4−, 5 mM HCO3−, 25 mM HEPES); impermeants to counteract cell swelling (100 mM lactobionate, 20 mM sucrose, 20 mM mannitol); colloid (6% Dextran-40); and metabolites (5 mM glucose, 2 mM adenosine, 3 mM glutathione).

Preservation of the pharmaceutical composition may also be achieved according to the invention by cryopreservation in dimethylsulfoxide (DMSO). This offers the advantage of allowing even longer shelf-life (one week or more) provided transportation on dry ice, with proper control of transportation temperature.

According to the embodiment of the pharmaceutical composition of the present invention wherein the excipient is HypoThermosol-FRS, the shelf-life of the pharmaceutical product a container is at least 72 hours. It is particularly remarkable to observe that a total number of $1200 \times 10^6$ cells have a volume of about 8 milliliters, whereas the maximum desirable volume for intramyocardial injection is about 10 milliliters. This means that the quantity of HypoThermosol-FRS is small vis-à-vis the cellular volume and will be in the range of only a few milliliters.

It has surprisingly been observed that even such a small quantity of HypoThermosol-FRS is sufficient to maintain such an important shelf-life of 72 hours for the pharmaceutical composition. This provides for sufficient time to confirm all release criteria are met, to ship the pharmaceutical composition anywhere in the world, and to deliver it to the recipient.

Pharmaceutical composition release criteria—Identity: Cardiopoietic cells are characterized by positive expression and, when applicable, nuclear translocation of several markers of early cardiac differentiation, including NRx2.5, MEF2C and GATA-4. Positive identity of cardiopoietic cells contained in the pharmaceutical composition is represented by a minimum 2-fold increase in expression level for MEF2C and/or Tbx5 compared to the reference standard, measured by real-time quantitative RT-PCR (qPCR) and maintenance thereof during shelf-life.

In this preferred embodiment, Table 1, Table 2 and Table 3 below show the expression of early cardiac differentiation markers is maintained for as long as 14 days after the pharmaceutical composition is stored in its final container, and that viability and proliferation of such cells is maintained for at least 5 days. This demonstrates the unique capacity of the manufacturing process hereby described to obtain and maintain the identity of the cells exposed to the cardiogenic substances in a state suitable for their intended use.

TABLE 1

Identity (qPCR) at 100 million total viable cells per ml.

| Day | Batch 1 MEF2C | Batch 1 Tbx5 | Batch 2 MEF2C | Batch 2 Tbx5 |
|---|---|---|---|---|
| 0 | 2.5 | 2.6 | 3.0 | 2.0 |
| 1 | 2.1 | 2.4 | 2.2 | 1.7 |
| 2 | 2.5 | 2.6 | 2.6 | 2.0 |
| 3 | 2.2 | 2.1 | 2.9 | 1.9 |
| 4 | 2.3 | 2.5 | 2.3 | 3.0 |
| 5 | 2.0 | 1.8 | 2.5 | 2.0 |
| 6 | 2.3 | 1.0 | 2.7 | 1.7 |
| 10 | 2.1 | 2.0 | 3.0 | 3.1 |
| 14 | 2.3 | 1.5 | 3.5 | 2.6 |

TABLE 2

Viability of the pharmaceutical composition at cellular concentration of 100 million total viable cells/ml.

| Day | Batch 1 | Batch 2 |
|---|---|---|
| 0 | 96 | 96 |
| 1 | 88 | 95 |
| 2 | 92 | 96 |
| 3 | 87 | 93 |
| 4 | 91 | 96 |
| 5 | 87 | 91 |

TABLE 3

Proliferative capacity of the pharmaceutical composition at cellular concentration of 100 million total viable cells/ml.

| Day | Batch 1 | Batch 2 |
|---|---|---|
| 1 | 444 | 456 |
| 2 | 297 | 481 |
| 3 | 417 | 333 |
| 4 | 306 | 417 |
| 5 | 303 | 722 |

Furthermore, Table 4 and Table 5 show that the pharmaceutical composition is not limited to a singly defined cell concentration yield. Indeed, maintenance of cell viability and proliferative capacity at different cellular concentrations are distinguishing features of the pharmaceutical composition hereby described.

TABLE 4

Influence of cell concentration on percent viability

| | Batch 1 (in Mio cells/ml) | | | Batch 2 (in Mio cells/ml) | |
|---|---|---|---|---|---|
| Day | 80 | 100 | 110 | 100 | 120 |
| 0 | 96 | 96 | 96 | 96 | 96 |
| 1 | 90 | 88 | 91 | 95 | 94 |
| 2 | 90 | 92 | 90 | 96 | 87 |
| 3 | 90 | 87 | 88 | 93 | 93 |
| 4 | 94 | 91 | 90 | 96 | 96 |
| 5 | 90 | 87 | 88 | 91 | 94 |

TABLE 5

Influence of cell concentration on proliferative capacity

| | Batch 1 (in Mio cells/ml) | | | Batch 2 (in Mio cells/ml) | |
| --- | --- | --- | --- | --- | --- |
| Day | 80 | 100 | 80 | 100 | 80 |
| 1 | 375 | 444 | 333 | 456 | 444 |
| 2 | 174* | 297 | 314 | 481 | 425 |
| 3 | 694 | 417 | 500 | 333 | 333 |
| 4 | 278 | 306 | 292 | 417 | 444 |
| 5 | 256 | 303 | 214 | 722 | 583 |

The value obtained for batch 1 at day 2 for 80 million cells per ml identified with (*) is considered an experimental error.

Pharmaceutical composition release criteria—Homogeneity: In order to determine the percentage of cardiopoietic cells in the pharmaceutical composition hereby described in this preferred embodiment, dual-immunolabelling is performed on an aliquot of cells with antibodies against MEF2C and CD105, followed by nuclear staining using DAPI. The goal is to determine the percentage of cardiopoietic cells (nuclear staining for MEF2C) and mesenchymal stem cells (CD105-positive), with the total number of counted cells given by the number of DAPI-stained nuclei. Analysis of patient-derived cardiopoietic cells that passed the identity test by qPCR (MEF2C, 2.8±0.6 fold increase, Tbx5: 2.2±0.6 fold increase) shows that 96±2% of the cells are cardiopoietic. In addition, 100% of the counted cells are CD105-positive. Taken together with the lack of increase in the level of expression of CD34, a marker for hematopoietic cells and endothelial progenitor cells (see paragraph on 'Purity'), this indicates that 100% of the cells are mesenchymal stem cells or derived from mesenchymal stem cells.

Pharmaceutical composition release criteria—Purity: The purity test performed according to the preferred embodiment of this invention aim at determining that cell types different from cardiopoietic cells and BMMSCs are absent from the pharmaceutical composition. A method of choice to address purity criteria is qPCR. The approach taken to develop the qPCR method for purity testing included the identification of suitable markers, design of proprietary primer and probe sets, analysis of amplification curves and melting peaks, and identification of commercially available positive control RNAs. Absence of the hematopoietic phenotype and of the endothelial progenitor phenotype both normally present in bone marrow is determined by the absence of detectable levels of CD34-expressing cells in the pharmaceutical composition. Absence of adipoblasts, chondroblasts, osteoblasts or neuroblasts is determined in the pharmaceutical composition by the absence of detectable levels of FABP4-expressing cells, Sox9-expressing cells, osteocalcin-expressing cells and nestin-expressing cells, respectively. Exclusion of mature cardiomyocytes is evaluated by the absence of detectable levels of MYH7-expressing cells in the pharmaceutical composition.

The herein described preferred embodiment for the pharmaceutical composition of the invention was injected endocardially in a human with heart failure of ischemic origin in an efficient amount of $1200 \times 10^6$ cells into the in the border zone of the non-viable myocardium using a dedicated catheter. Satisfactory results were obtained.

The feasibility, safety and efficacy of a pharmaceutical composition containing cardiopoietic cells, according to the invention, was evaluated in a prospective, randomized, open, sequential parallel two-armed, multi-centre clinical trial.

Subjects presenting with chronic heart failure secondary to ischemic cardiomyopathy were randomly assigned to the control or treated group. The control group received optimal standard of care. The treated group received the pharmaceutical composition containing cardiopoietic cells in addition to optimal standard of care.

The pharmaceutical composition containing cardiopoietic cells was injected endoventricularly in the border zone of the infracted area using the MyoStar® Injection Catheter (Biologics Delivery Systems, California, USA). In a single injection procedure, up to $1.2 \times 10^9$ cells were injected in up to twenty injection sites surrounding the infarcted area.

Two-dimensional echocardiographic evaluation of left ventricular (LV) function was performed in 17 subjects enrolled in this trial (9 treated, 8 control) at baseline and at 6 months thereafter. Cardiac function was assessed by measuring the change in LV End Diastolic Volume (LVEDV), LV End Systolic Volume (LVESV), and LV Ejection Fraction (LVEF) from baseline to 6 month post-cell injection. A trend was observed for these three important parameters in the treated group in favour of a positive effect of the pharmaceutical composition on the cardiac function (FIG. 1). Physician skilled in the art would recognize the important prognostic and therapeutic implications these results carry.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

In particular, the pharmaceutical composition described herein, including its storage conditions and shelf-life, is only a preferred embodiment that depicts use of autologous cardiopoietic cells derived from bone marrow mesenchymal stem cells (BMMSCs), i.e. a pharmaceutical composition prepared from BMMSCs to be used in the same individual the BMMSCs were collected from. The scope the present invention is not limited to autologous BMMSCs and includes use of any stem cells, irrespective of the source. Cells which allow to obtain cells committed to the generation of heart tissue (herein after in this paragraph 'original cells') may be allogeneic and xenogenic. Original cells may also be obtained by other means than fresh bone marrow procurement. Original cells may be embryonic stems cells provided that their procurement does not involve destruction of human embryos. Original cells can be embryonic-like stem cells such as Induced Pluripotent Stem (IPS) cells obtained by any means including transfection, cellular reprogramming or other method which renders IPS free of exogenous genes. Original cells can also be Marrow-Isolated Adult Multilineage Inducible (MIAMI) cells, resident cardiac stem cells, vegetal stem cells, or any combination thereof. The subject invention is not limited to specific formulation components, manufacturing methods, biological materials or reagents, dosage regimens and the like, as such may vary.

In a further embodiment, the pharmaceutical composition described herein may include additional components for example cardiogenic substances, growth factors such as fibroblast growth factors, placental growth factor or vascular endothelial growth factor, cytokines, or proteins involved in organogenesis signalling, molecular constructs, non-cardiopoietic cells altered ex vivo, pharmaceuticals, platelet lysate, scaffold materials such as collagen, laminin, or any other extracellular matrix proteins.

In a further embodiment, the kit described herein may include a catheter according to PCT/EP2010/055869, TW099113613, U.S. 61/312,371, BE2009/0271, PCT/EP2010/055856, TW099113627, or BE2009/0272.

In a further embodiment, the kit described herein may include additional components for instance bags or media suitable for refrigeration, freeze, cryopreservation, lyophilisation, vitrification, thawing, rehydration, washing, sorting, concentration, filtering, lyophilisation, centrifugation, resuspension, sampling, or aliquoting the pharmaceutical composition.

In a further embodiment, the kit described herein may include thermomonitoring, anti-tamper device, or radiofrequency identification device.

It is also to be understood that the terminology used herein is for the purpose of describing particular embodiments only and is not intended to be limiting.

The invention claimed is:

1. A pharmaceutical composition comprising intermediate phenotype cells committed to the generation of heart tissue, wherein said cells show:
   i) an observed increase in expression level of both MEF2C and at least one further gene selected from the group consisting of:
      Nkx2.5, Tbx5, GATA4, GATA6, Mesp1, FOG1 FOG2, Flk1 and homologues thereof;
      as compared to a non-cardiopoietic reference; and
   ii) an absence of detectable levels of MYH7 expression; and
at least one pharmaceutically acceptable excipient, wherein said at least one pharmaceutically acceptable excipient is a preservation solution which comprises dimethylsulfoxide (DMSO), ions, pH buffers, impermeants, colloids, and metabolites;
wherein the contents of total non-cardiopoietic cells is between 0% and 50% of the total number of cells.

2. The pharmaceutical composition of claim 1, wherein the preservation solution is chosen in the group comprising preservation solutions which allow cryopreservation at temperatures between −196° C. and 0° C. and preservation solutions which allow preservation at temperatures between 0° C. and +40° C.

3. The pharmaceutical composition of claim 1, wherein the preservation solution is a preservation solution which further contains one or more components selected from the group consisting of glycerol, sucrose, serum albumin, trehalose, and combinations thereof.

4. The pharmaceutical composition of claim 1, wherein said ions are selected from the group consisting of $Na^+$, $K^+$, $Ca^{2+}$, $Mg^{2+}$, $Cl^-$ and combinations of said ions.

5. The pharmaceutical composition of claim 1, wherein said pH buffers are selected from the group consisting of $H_2PO_4^-$, $HCO_3^-$, (4-(2-hydroxyethyl)-1-piperazineethanesulfonic acid) (HEPES) and mixtures thereof.

6. The pharmaceutical composition of claim 1, wherein said impermeants are selected from the group consisting of lactobionate, sucrose, mannitol, glucose and combinations thereof.

7. The pharmaceutical composition of claim 1, wherein said colloid is Dextran-40.

8. The pharmaceutical composition of claim 1, wherein said metabolites are selected from the group consisting of adenosine, glutathione, and combinations thereof.

9. The pharmaceutical composition of claim 1, wherein said at least one pharmaceutically acceptable excipient comprises at least one component selected from the group consisting of growth factors, cytokines, proteins involved in organogenesis signalling, pharmaceuticals, platelet lysate, serum, isotopes, means for tracing cells in vivo, diluents, lubricants, matrix or scaffold materials, and combinations thereof.

10. The pharmaceutical composition of claim 1, wherein said cells committed to the generation of heart tissue are stem cells.

11. The pharmaceutical composition of claim 10, wherein said stem cells are selected from the group consisting of adult stem cells, embryonic stem cells, induced pluripotent stem cells (IPS), marrow-isolated adult multilineage inducible cells (MIAMI), resident cardiac stem cells, vegetal stem cells, and combination thereof.

12. The pharmaceutical composition of claim 11 wherein said stem cells are mesenchymal stem cells harvested from a suitable tissue source selected from the group consisting of bone marrow, adipose tissue, umbilical cord blood, amniotic fluid, menstrual fluid, and blood.

13. The pharmaceutical composition of claim 1, wherein said cells committed to the generation of heart tissue derive from stem cells.

14. The pharmaceutical composition of claim 1, wherein said cells committed to the generation of heart tissue are mammalian cells.

15. The pharmaceutical composition of claim 14, wherein said mammalian cells selected from the group consisting of humans, cats, dogs, pigs, horses, mice, rats, and hamsters.

16. The pharmaceutical composition of claim 1, wherein said cells are autologous cells, allogeneic cells, xenogenic cells, or any combination thereof.

17. The pharmaceutical composition of claim 1, wherein said cells committed to the generation of heart tissue are cardiopoietic cells which can be derived from human adult mesenchymal stem cells, human embryonic stem cells (provided their production implies no human embryo destruction), embryonic-like stem cells, inducible pluripotent stem cells, cardiac resident stem cells or any other adapted source or combination thereof.

18. The pharmaceutical composition of claim 17, wherein said composition contains no detectable non-cardiopoietic cells, including but not limited to cardiomyocytes, hematopoietic cells, endothelial progenitor cells, adipoblasts, adipocytes, chondroblasts, chondrocytes, osteoblasts osteocytes, neuroblasts and neurocytes.

19. The pharmaceutical composition of claim 18, wherein the contents of each category of non-cardiopoietic cells is between 0% and 50% of the total number of cells.

20. The pharmaceutical composition of claim 18 wherein the contents of total non-cardiopoietic cells is between 0% and 15% of the total number of cells.

21. The pharmaceutical composition of claim 18 wherein the contents of each category of non-cardiopoietic cells is between 0% and 15% of the total number of cells.

22. The pharmaceutical composition of claim 1 for use for the treatment of ischemic cardiomyopathy, acute myocardial infarction, chronic myocardial infarction, heart failure of non-ischemic origin, heart failure of ischemic origin, congenital cardiomyopathy, or combination thereof.

23. The pharmaceutical composition of claim 1, wherein the observed increase in expression level is a minimum of 2-fold as determined by qPCR, as compared to a reference.

24. A pharmaceutical composition comprising:
intermediate phenotype cells committed to the generation of heart tissue, wherein said cells show an observed presence of
  i) at least one polypeptide species chosen from the group consisting of: Nkx2.5; Tbx5; GATA4; gATA6; Mesp1; FOG1; FOG2; Flk1; and homologoues thereof;
  as compared to a non-cardiopoietic reference;
  ii) nuclear translocation to the nuclei of the cell of one or more of Nkx2.5 and MEF2C; and
an absence of detectable levels of MYH7 expression; and
at least one pharmaceutically acceptable excipient, wherein said at least one pharmaceutically acceptable excipient is a preservation solution which comprises dimethylsulfoxide (DMSO), ions, pH buffers, impermeants, colloids, and metabolites;
wherein the contents of total non-cardiopoietic cells is between 0% and 50% of the total number of cells.

25. A method for the treatment of heart disease disorders or predisposition of a disorder wherein the pharmaceutical composition of claim 1 is delivered into an individual in an effective amount.

26. The method of claim 25, wherein the individual suffers from a condition selected from one or more of the group consisting of ischemic cardiomyopathy, myocardial infarction, heart failure of ischemic origin, heart failure of non-ischemic origin, congenital cardiomyopathy, and combinations thereof.

27. The method of claim 25, wherein the pharmaceutical composition is delivered using a route of administration selected from the group consisting of intra-myocardial, intra-cardiac, intra-coronary, intra-muscular, sub-cutaneous, intra-peritoneal, in utero, parenteral, or systemic.

28. The method of claim 25, wherein the pharmaceutical composition is delivered intramyocardially using a catheter.

29. The method of claim 25, wherein the pharmaceutical composition is delivered intramyocardially using a syringe.

30. A kit for the administration of a pharmaceutical composition of claim 1 which kit comprises a container containing said pharmaceutical composition.

31. The kit of claim 30 wherein said container is a biocompatible container that allows cell survival and transportation worldwide, convenient handling by health care provider or staff for delivery to a recipient.

32. The kit of claim 30, wherein said container is hermetically closed.

33. The kit of claim 30, wherein said container is compatible with the excipient and conditions of preservation.

34. The kit of claim 30, wherein said container is a closed glass container.

35. The kit of claim 30, wherein said container has a piercable septum cap.

36. The kit of claim 35 wherein said piercable septum cap is configured so as to allow a vial adapter, which adapter includes a luer activated valve, to draw fluid from the container.

37. The kit of claim 36 wherein the said piercable septum cap can be accessed with a needle.

38. The kit of claim 30, wherein the said pharmaceutical composition is stored in a hermetically closed container suitable for cryopreservation.

39. The kit of claim 30, wherein shelf-life of pharmaceutical composition in said container is at least 48 hours.

40. The kit of claim 30, wherein the shelf-life of the pharmaceutical composition in said container is at least 72 hours.

41. The kit of claim 30, which further comprises at least one catheter.

42. The kit of claim 30, which further comprises at least one syringe.

\* \* \* \* \*